(12) United States Patent
Wilkins et al.

(10) Patent No.: US 7,196,116 B1
(45) Date of Patent: Mar. 27, 2007

(54) SOLID PESTICIDE COMPOSITIONS WITH EXTENDED STABILITY

(75) Inventors: Frances Chandler Wilkins, Highland Village, TX (US); Joe Doyle McDaniel, Carrollton, TX (US); Kim W. Yang, Dallas, TX (US)

(73) Assignee: Wellmark International, Schaumburg, IL (US)

( * ) Notice: Subject to any disclaimer, the term of this patent is extended or adjusted under 35 U.S.C. 154(b) by 81 days.

(21) Appl. No.: 11/150,356

(22) Filed: Jun. 10, 2005

Related U.S. Application Data

(63) Continuation-in-part of application No. 10/828,657, filed on Apr. 20, 2004.

(51) Int. Cl.
*A01N 37/06* (2006.01)

(52) U.S. Cl. ............... 514/549; 424/405; 424/406; 424/408; 424/409; 523/122

(58) Field of Classification Search ............... 424/408, 424/409, 125
See application file for complete search history.

(56) References Cited

U.S. PATENT DOCUMENTS

| 4,732,762 A | 3/1988 | Sjogren |
| 4,876,091 A | 10/1989 | Clarke, Jr. |
| 6,346,262 B1 * | 2/2002 | Levy .................. 424/408 |

* cited by examiner

*Primary Examiner*—Neil S. Levy
(74) *Attorney, Agent, or Firm*—Townsend and Townsend and Crew LLP

(57) ABSTRACT

Compositions and methods are disclosed which greatly improve the shelf-life of pesticidal agents and especially insecticides. The tendency of the composition to segregate from the solid components is minimized, which improves uniformity throughout the product.

15 Claims, 3 Drawing Sheets

A

B

C

SOLID PESTICIDE COMPOSITIONS WITH EXTENDED STABILITY

CROSS-REFERENCES TO RELATED APPLICATIONS

This application is a continuation-in-part to U.S. application Ser. No. 10/828,657, filed Apr. 20, 2004, the teaching of which is hereby incorporated by reference in its entirety for all purposes.

BACKGROUND OF THE INVENTION

The Environmental Protection Agency (EPA) sets certified limits for a pesticide product. Certified limits are required for each active ingredient, each inert ingredient, and, if the product is a technical product, each impurity of the pesticide product. The certified limits set standard concentration ranges for each of the foregoing components within the pesticide product. If, for example, the active ingredient is outside the certified limits, the pesticide product expires and cannot be used or sold.

There is a need in the art for pesticide products with extended shelf-lives that maintain certified limits. The present invention satisfies this and other needs.

BRIEF SUMMARY OF THE INVENTION

The compositions and methods of the present invention greatly improve the shelf-life stability of pesticide formulations (e.g., methoprene). In particular, the inventive compositions and methods of the present invention improve on process controls of the pesticide such that the tendency to segregate from solid components is minimized, which increases uniformity throughout the product.

As such, in one aspect, the present invention provides a pesticide composition comprising a pesticidal agent on a solid carrier; a biopolymer; and an effective amount of a plaster of paris to harden the composition, wherein the pesticidal agent maintains certified limits for at least 12 months.

In another aspect, the present invention provides a method for making a pesticide composition comprising:

(a) preparing a pesticidal agent on a solid carrier;
(b) premixing water, a surfactant, and a biopolymer to form an aqueous premix;
(c) dispersing the pesticidal agent on a solid carrier within the aqueous premix to form a dispersed mixture;
(d) adding a plaster of paris to the dispersed mixture to form a slurry; and
(e) molding the slurry to form the pesticide composition.

The methods of the present invention improve the use of solid pesticide premixes in various geometric forms, such as large and small cork shaped briquets, pellets, cubes, blocks, ingots, torpedoes, and the like.

In another embodiment, the compositions and methods of the present invention improve the hardness of the finished product. The increased hardness improves protection of the pesticide from reacting with other components and ingredients found in the environment, such as, for example, water gardens, fountains, water troughs, and the like. The solid formulations of the present invention have a "crushing" or "tensile" strength, which is defined as the force required to break a solid formulation by compression in the radial direction, which is higher than previously known formulations.

In yet another embodiment, the process improvements recited herein have reduced the amount of waste generated and allow for better control of the formation of the solid product. The formulations of the present invention also allow the adjustment of the rate of release of the active ingredient(s) without the need for adjusting the nominal level of the active ingredient(s). Advantageously, the formulations and methods of the present invention are particularly effective against mosquitoes such as *Culex quinquefasciatus*, which are known to carry the West Nile virus.

In another embodiment, the present invention provides a method for controlling a pest, comprising: contacting the pest with a pesticide composition comprising: a pesticidal agent on a solid carrier; a biopolymer; and an effective amount of a plaster of paris to harden said composition, wherein the pesticidal agent maintains certified limits for at least 12 months, to thereby control the pest.

These and other objects, advantages, and features will become more apparent when read with the detailed description and drawings which follow.

DETAILED DESCRIPTION OF THE INVENTION

I. General

Figure 1:
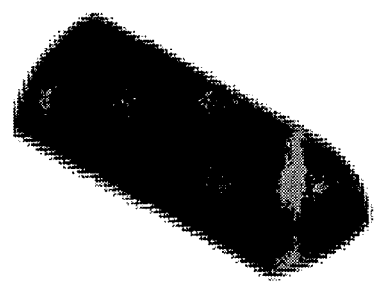
FIG. 1 A–C show geometric shapes of embodiments of the present invention, A) Ingot; B) Briquet; and C) Cork.
Figure 1:
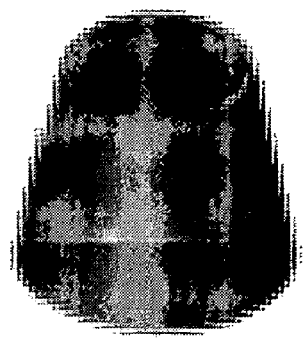
Figure 1:
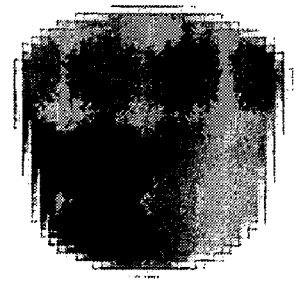

Under 40 C.F.R. § 158.175, the EPA sets forth certified limits for the concentrations of the active and inert ingredients found in a pesticide product. The certified limits represent a range with both upper and lower limits. The table of standard certified limits as set forth in the foregoing regulation is shown in Table 1.

TABLE 1

Standard Certified Limits

| If the nominal concentration (N) for the ingredient is: | The certified limits for that ingredient will be as follows: | |
| --- | --- | --- |
|  | Upper Limit | Lower Limit |
| $N \leq 1.0\%$ | $N + 10\% N$ | $N - 10\% N$ |
| $1.0\% < N \leq 20.0\%$ | $N + 5\% N$ | $N - 5\% N$ |
| $20.0\% < N \leq 100.0\%$ | $N + 3\% N$ | $N - 3\% N$ |

Advantageously, the pesticide products and compositions of the present invention have increased shelf-lives, as the pesticidal agents are stable longer. That is, the pesticidal agent maintains certified limits for at least 12 months, more preferably at least 18 months and as long as 2 years, or even 36 months or yet even longer. This is a surprising advancement over the art.

II. Pesticides

Various pesticides or pesticidal agents are suitable for use in the present invention. The term "pesticidal agent" or "pesticide" as employed herein is intended to include any active material used for the control of unwanted plants, animals, or microorganisms, such as mosquitoes, fungi, algae, snails, and weeds. Suitable pesticidal agents include, without limitation, insecticides, biocides, herbicides, fungicides, and other materials utilizable in the environment.

In a preferred aspect, the pesticidal agent of the present invention is an insect growth regulator (IGR). Insect growth regulators, including juvenile hormones, are well known for their use and efficacy in controlling or eliminating insect infestation in humans, in animals, and in both residential and industrial environments. Many types of insects are controllable by insect growth regulators, including, without limitation, flies (e.g., face flies, house flies, stable flies, and horn flies), fleas, mosquitoes, flour beetles, cigarette beetles, and cockroaches.

The insect growth regulators vary widely in chemical composition, with two of the more prominent classes comprising 2,4-dienoic acids and phenoxyphenoxy compounds, e.g., phenoxyphenoxyalkoxyheterocyclics. Benzoylureas and triazine derivatives are also suitable for use in the present invention as insect growth regulators. Examples of 2,4-dienoic acids and related compounds include, without limitation, methoprene, hydroprene, neotenin, and epiphenonane. As used herein, "methoprene" includes R-methoprene, S-methoprene, and all mixtures of R- and S-methoprene. S-methoprene is the preferred methoprene. Examples of phenoxyphenoxy compounds include, without limitation, fenoxycarb and pyriproxyfen. Examples of benzoylureas include, without limitation, lufenuron, diflubenzuron, terflubenzuron, triflumaron, hexaflumaron, and flucycloxuron. An example of a triazine derivative is 2-cyclopropylamino-4,6-bis(dimethylamino)-s-triazine.

Suitable IGRs for use in the present invention include, without limitation, chitin synthesis inhibitors such as bistrifluron, buprofezin, chlorfluazuron, cyromazine, diflubenzuron, flucycloxuron, flufenoxuron, hexaflumuron, lufenuron, novaluron, noviflumuron, penfluron, teflubenzuron, and triflumuron; juvenile hormone mimics such as epofenonane, fenoxycarb, hydroprene, kinoprene, methoprene, pyriproxyfen, and triprene; juvenile hormones such as juvenile hormone I, juvenile hormone II, and juvenile hormone III; molting hormone agonists such as chromafenozide, halofenozide, methoxyfenozide, and tebufenozide; molting hormones such as α-ecdysone and ecdysterone; molting inhibitors such as diofenolan; precocenes such as precocene I, precocene II, and precocene III; unclassified insect growth regulators such as dicyclanil; other IGRs; and mixtures thereof. Preferred IGRs include, for example, methoprene, hydroprene, kinoprene, fenoxycarb, pyriproxifen, and mixtures thereof. In a particularly preferred embodiment, the IGR is methoprene.

In certain aspects, the ratio of pesticide (e.g., S-methoprene) in the formulation is from about 0.002 w/w to about 40 w/w. Preferably, the ratio of pesticide in the formulation is from about 0.01 w/w to about 20 w/w, and more preferably, about 0.01 w/w to about 10 w/w.

III. Carriers

In certain aspects, the pesticidal agent of the present invention comprises a carrier such as a solid carrier. Solid carriers, which can be manufactured or formulated for dusts, wettable powders, water dispersible granules, or granules, may be mineral fillers, such as calcite, silica, talc, kaolin, carbon, charcoal, montmorillonite, or attapulgite. The physical properties can be improved by the addition of highly dispersed carbon, silica gel, or polymers. Carriers for granules may be a porous material, e.g., pumice, kaolin, sepiolite, or bentonite; non-sorptive carriers include calcite and sand. Additionally, a multitude of pre-granulated inorganic or organic materials may be used, such as dolomite or crushed plant residues. Other suitable carriers include, but are not limited to, silica gel, sand, gypsum, carbon, charcoal, and combinations thereof.

A practical material for the carrier of the pesticide is a fine carbon in a matrix of plaster of paris, which forms a gypsum-type product. The pesticide is sprayed onto fine carbon particles and intimately bonded with the plaster of paris and is released when water dissolves the solid gypsum. Gypsum-based pesticides are known in the art; for example, the product known as ALTOSID®, made by Wellmark International (Schaumberg, Ill.), uses methoprene.

In certain aspects, the compositions of present invention have a ratio of pesticide to solid carrier from about 0.001 w/w to about 30.0 w/w. Preferably, the ratio of pesticide to solid carrier is from about 0.01 to about 10.0 w/w.

In certain other aspects, the formulations of the present invention are solid formulations. Such solid formulations can be in a variety of forms including, but not limited to, cork-shaped briquets, cubes, pellets, blocks, ingots, torpedoes, and other geometries.

Pesticidal compositions are often formulated and transported in a concentrated form which is subsequently diluted by the user before application. The presence of small amounts of a carrier which is a surfactant facilitates this process of dilution. Thus, a carrier in the formulations according to the invention can comprise a surfactant. For example, the formulations can contain at least two or more carriers, at least one of which is a surfactant.

Surfactants can be nonionic, anionic, cationic or zwitterionic substances with good dispersing, emulsifying, and wetting properties, depending on the nature of the pesticide compound. Surfactants can also refer to mixtures of individual surfactants. Suitable surfactants for use in the present invention include, without limitation, a nonionic ethoxylated alcohol, an ethoxylated substituted phenol, and a mixture thereof.

In certain instances, the preferred carrier is plaster or gypsum. Dehydration of gypsum (i.e., calcium sulfate dihydrate, $CaSO_4 \cdot 2H_2O$) in an open kettle by direct heating in the range of 390°–570° F. results in beta-calcium sulfate hemihydrate, $CaSO_4 \cdot \frac{1}{2}H_2O$, commonly referred to as plaster. Typically, the plaster crystals are long, needle-like, irregular in shape, and porous. The shape and porosity of the crystalline particles result in high water absorbency. The powder, when mixed with water, requires about 60 parts of water to about 100 parts of plaster to give a "workable" consistency. Plasters can contain a variety of additives which provide properties such as wetability, strength, hardening rate, particle size, low viscosity slurries, and the like.

Preferred plaster compositions having a controlled rate of erosion and/or slow release in the environment comprise plasters which slowly disintegrate over a time period of 120 to 180 days and can expose the pesticides into the environment during the erosion period. The compositions of the present invention maintain certified limits for at least 12 months, preferably at least 18 months, and more for preferably at least 24 months, and up to 36 months.

The most preferred plaster for making the pest (e.g., mosquito) control compositions of the present invention comprises a high density, high compressive strength plaster having a density of at least 1,600 grams per liter and a compressive strength of at least 5,000 lbs. per square inch, preferably 9,000 lbs. per square inch, and more preferably about 10,000–15,000 lbs. per square inch or greater, for reasons of its slow erosion and or slow release into the environment.

In certain preferred instances, the carrier is carbon. Suitable types of carbon useful for making the pest (e.g., mosquito) control compositions of the present invention include, for example, finely divided carbon compositions having a large surface area and a small particle size (e.g., carbon particles). Without being bound to any particular theory, it is believed that the carbon in the composition tends to smooth the release rate of the pesticidal agent (e.g., insecticide) by absorbing extra concentrations of the pesticidal agent when the release rate is high and by releasing or desorbing the pesticidal agent when the release rate is low. The carbon particles, in combination with the pesticidal agent, also appear to control the release locus of the pesticide. The carbon particles also protect the insecticide by absorbing ultraviolet radiation and preventing the deterioration of the insecticide through the effects of such radiation.

Accordingly, a preferred particulate carbon useful in the present invention has a large surface area and a small particle size and can be found in carbon sources such as activated carbon, finely divided charcoal, and the like. Further details of sources of finely divided carbon are found in Kirk-Othmer Encyclopedia of Chemical Technology, Second Edition, Volume IV, pages 149–335.

In a certain embodiment, the pest control composition is formed from an effective amount of a pest control compound with a sufficient amount of plaster to result in a slow dissolution of plaster lasting throughout the mosquito season (e.g., 140 days), a sufficient amount of charcoal to prevent decomposition of the insecticide and to smooth the release of the insecticide, a biopolymer (as described below) and a sufficient amount of water suitable in manufacture and to cause the mixture to form a solid object which can be distributed throughout the environment.

The pest control composition can take the form of a pest control means having essentially any regular or irregular three-dimensional shape including, but not limited to, spheres such as oblate spheres; polygons such as cubes, dodecahedrons, and pyramids; cylinders such as cones and truncated cones; pillows; briquets; coated cylinders such that erosion takes place at the ends, and the like.

The release rate of the pest control agent from the means (e.g., briquet) appears to be proportional to the means' surface area. The surface area should range from about 200 to about 50,000 $mm^2$, preferably about 1,500 to about 25,000 $mm^2$, and more preferably about 2,500 to about 7,500 $mm^2$, depending on the concentration of the pesticide to the means and for reasons of economy and ease of handling. The preferred form of the slow release composition is in the form of a cylinder having dimensions of about 10 to about 100 millimeters in diameter, and about 10 to about 100 millimeters in depth.

As is shown in FIG. 1A, in another preferred form, the slow release composition is in the form of an ingot having sloping sides. Preferably, the dimensions are about h=24 mm, l=73 mm, width 20 mm [top]–28 mm[bottom], having a mass of between 41–52 grams.

Turning now to FIG. 1B, a preferred embodiment of the pest control formulation for use with mosquito control is in the form of briquets having for example, a major diameter of about 30 to about 50 millimeters, a minor diameter of about 30 to about 35 millimeters, a height of about 35 to about 40 millimeters, a mass of about 41 to about 56 grams, and a total surface area of about 4,000 to about 8,000 $mm^2$.

In certain aspects, the surface area in sq. mm for the various shapes are as follows: for the Ingot (FIG. 1A): about 7200 $mm^2$ to about 7900 $mm^2$ such as 7426 $mm^2$ (41–52 g); the Briquet (FIG. 1B): about 2200 $mm^2$ to about 2900 $mm^2$ such as 2777 $mm^2$ (5.4–6.0 grams); for the cork (FIG. 1C): about 6200 $mm^2$ to about 6900 $mm^2$ such as 6798 $mm^2$; and the pellet: about 200 $mm^2$ to about 300 $mm^2$; such as 253 $mm^2$.

The compositions of the present invention can also be formed into objects having a substantial irregular shape; however, a sufficient amount of the composition should be included in the object so that a substantial pest control concentration of the insecticide composition is present in the environment throughout the substantial portion of the insect season.

The slow release pest control composition can comprise from about 50% to about 95%, preferably about 55% to about 80%, and more preferably about 60% to about 80% plaster, depending on the length of the temperate season. The slow release composition can comprise 80% by weight or less of a pest control agent, preferably 70% or less of a pest control agent, and more preferably, for reasons of economy, ease of handling, and effective pest control, the composition can contain about 1 to about 25% by weight, preferably about 2 to about 15% by weight, and more preferably, for reasons of efficient mosquito control throughout the season, about 3 to about 8% by weight of the pest control agent. The composition can comprise about 30% by weight, preferably about 5% to about 25% by weight, and more preferably 10% to about 20% such as 10%, 11%, 12%, 13%, 14%, 15%, 16%, 17%, 18%, 19%, and 20% by weight of charcoal or activated carbon in order to protect the insecticide and to control the release of the insecticide composition.

A sufficient amount of water is added to the mixture of dry components to hydrate the plaster to bind the components together so that the composition can be formed into objects which can be distributed in the environment. Typically, an amount of water in the range of about 25 to about 50% by weight of the composition can be present in the wet mix before molding.

IV. Biopolymers

In certain preferred aspects, the biopolymer suitable for use in the present invention is a carbohydrate (e.g., saccharide). Suitable carbohydrates include, without limitation, oligosaccharides, polysaccharides, and mixtures thereof. Suitable polysaccharides include, for example, a cyclodextrin, a starch, a carboxymethyl cellulose salt, an alginate, a methyl cellulose, an ethyl cellulose, a hydroxypropyl cellulose, sucrose, a starch glycolic acid salt, molasses, lactose, dextrin, acacia, agar, guar, locust bean, tragacanth, xanthan, and combinations thereof. In certain aspects, the saccharide is a water-soluble saccharide. In a preferred embodiment, the shelf-life extending agent is molasses. Suitable types of molasses include, but are not limited to, beet sugar molasses, citrus molasses, hemicellulose extract, starch molasses, cane sugar molasses, and combinations thereof. Those of skill in the art will know of other types of molasses suitable for use in the present invention.

In certain other aspects, the shelf-life extending agent is a cyclodextrin, such as an amorphous cyclodextrin as disclosed in U.S. Pat. No. 4,727,064, incorporated herein by reference. As disclosed therein, a cyclodextrin-based mixture can be prepared from α-, β-, or γ-cyclodextrin, which can be rendered amorphous through non-selective alkylation. The alkylation agents suitable for non-selective alkylation are exemplified by propylene oxide, glycidol, iodoacetamide, chloroacetate, and 2-diethylaminoethylchloride. The reaction between an alkylation agent and a cyclodextrin can be performed to yield mixtures containing many components, which effectively prevents crystallization processes within the above pharmaceutical preparation.

In certain instances, such as in a solid formulation, the ratio of pesticide to biopolymer is from about 1:1000 to about 1:1 w/w, preferably from about 1:500 to about 1:50 w/w, and more preferably from about 1:50 to about 1:25 w/w.

In certain other instances, such as in a solid formulation, the ratio of pesticide to biopolymer is from about 1000:1 w/w, preferably from about 500:1 to about 1:1 w/w, and more preferably from about 75:1 to about 1:1 w/w, such as 75:1, 70:1, 65:1, 60:1, 55:1, 50:1, 45:1, 40:1, 35:1, 30:1, 25:1, 20:1, 15:1, 10:1, 5:1, 1:1, as well as integers and fractional integers between 75:1 and 1:1.

In certain other instances, the compositions further comprise a binding agent.

In certain additional instances, the pesticide composition further comprises an antioxidant. Suitable antioxidants include, but are not limited to, Vitamin E, Vitamin A palmitate, ethoxyquin, propyl gallate, butylated hydroxyanisole (BHA), butylated hydroxytoluene (BHT), and combinations thereof.

Surprisingly, the biopolymer imparts a "crushing" or "tensile" strength which is higher than the prior art formulations. This advantageous property extends the shelf-life and thus prolongs the stability of the pesticide compositions.

V. Methods of Making

In one embodiment, the present invention provides a method of making a pesticide composition comprising:
    (a) preparing a pesticidal agent on a solid carrier;
    (b) premixing water, a surfactant, and a biopolymer to form an aqueous premix;
    (c) dispersing the pesticidal agent on a solid carrier with the aqueous premix to form a dispersed mixture;
    (d) adding a plaster of paris to the dispersed mixture to form a slurry; and
    (e) molding the slurry to form the pesticide composition.

In certain aspects, the compositions of the present invention are made by preparing a pesticidal agent (such as S-methoprene) on a solid carrier (such as carbon) such as by spray drying S-methoprene onto carbon particles. Next, water, a surfactant such as a nonionic ethoxylated alcohol, and a biopolymer such as a biopolymeric gum, are mixed to form an aqueous premix. Suitable surfactants for use in the present invention include, without limitation, a nonionic ethoxylated alcohol, an ethoxylated substituted phenol, and a mixture thereof. Thereafter, the S-methoprene on carbon particles is dispersed within the aqueous premix to form a dispersed mixture. Plaster of paris is then added to the dispersed mixture to form a slurry. The slurry is then molded to form the pesticide composition. Typically, an amount of water in the range of about 25 to about 50% by weight of the composition can be present in the wet mix before molding.

In still other aspects, the present invention provides aqueous dispersions and emulsions such as, for example, compositions obtained by diluting the formulated product with water.

In further aspects, the biological activity of the active ingredient can be increased by including an adjuvant. An adjuvant is defined herein as a substance which can increase the biological activity of an active ingredient but is not itself significantly biologically active. The adjuvant can either be included in the formulation as a co-formulant or carrier, or can be added to the formulation containing the active ingredient.

VI. Uses

The control of insect populations can be maintained over varying time frames, depending on the insect season and the surface area and composition of the object distributed in the environment. Protection can be maintained for as little as 5 to 30 days and for as long as 150 days. An object having from 10 to 20 grams of material can provide pest control for 30 to 80 days. A pest control means object having from about 25 to 40 grams can provide a controlling amount of pest control agent for 80 to 150 days.

The pest control means (e.g., an ingot shaped methoprene composition unit) can be applied to a site at a rate of about 100 to 600 means per acre, preferably about 300 to 500 means per acre, and more preferably about 400 to 450 means per acre. Commonly, the spacing of the pest control means at the breeding site can be about 1 to 30 feet between briquets, preferably about 5 to 25 feet, and more preferably about 7 to 12 feet. The even distribution of the briquet can be important in controlling mosquitoes through likely breeding territories where the topography is substantially unknown. In certain areas where the topography is more familiar, such a uniform distribution scheme is not absolutely necessary. In large areas of known topography where substantial water accumulates, it is important to introduce a sufficient number of the pest control means to provide a pest controlling amount of pesticide to the water. However, the pest control means do not have to be uniformly distributed.

The pest control means can be distributed into the environment by hand, from ground vehicles or boats, by helicopter or other aircraft, or by any other means insuring a fairly even distribution of the pest control means into the environment. The pest control means of the invention can be distributed into any environmental location which is seasonally flooded or contains standing water during a substantial portion of the season. Typical wetland areas which can be treated using the pest control means of the invention are seasonally flooded basin or flat sites typical of woodland areas having few aquatic plants or grasses. Such sites generally are flooded during the wetter periods of the temperate season. The pest control means can also be used in any of a variety of other wetland areas such as, for example, inland fresh meadow areas that contain standing water for greater periods of time during the year and are commonly characterized by the presence of reeds, canary grass, or other plants common in a wetter environment; inland shallow fresh water marshes that are commonly muddy throughout the growing season with about 6 inches of water, commonly characterized by the presence of cattail ranks and grass across geographically depressed areas; inland deep water, fresh water marshes that commonly have water all year round, with pockets of open water permitting submerged aquatic plants to grow, and can have as much as six inches to three feet of water permanently present; inland open fresh water such as game lakes that commonly have fresh water present at depths of greater than 10 feet, and can be characterized by depths free of vegetation, while vegetation is commonly present in the shallows or at the water edge. The pest control means can be used in any of the above wetland areas in order to control pest populations. Mosquitoes, for example, are most commonly produced in areas that are seasonally flooded or where the water depth fluctuates.

The pest control means can be applied to an environment that is substantially dry or wet. In a dry environment (no standing water) atmospheric humidity will result in little or no pesticide release. In wet environments (standing water) where the pest control means is immersed, water that induces erosion and/or slow release will generally be environmental standing water. One skilled in the art understands that decomposition is generally favored and is most efficient in the presence of standing water.

VII. EXAMPLES

The following examples are offered to illustrate, but not to limit, the claimed invention.

Example 1

Figure 2:
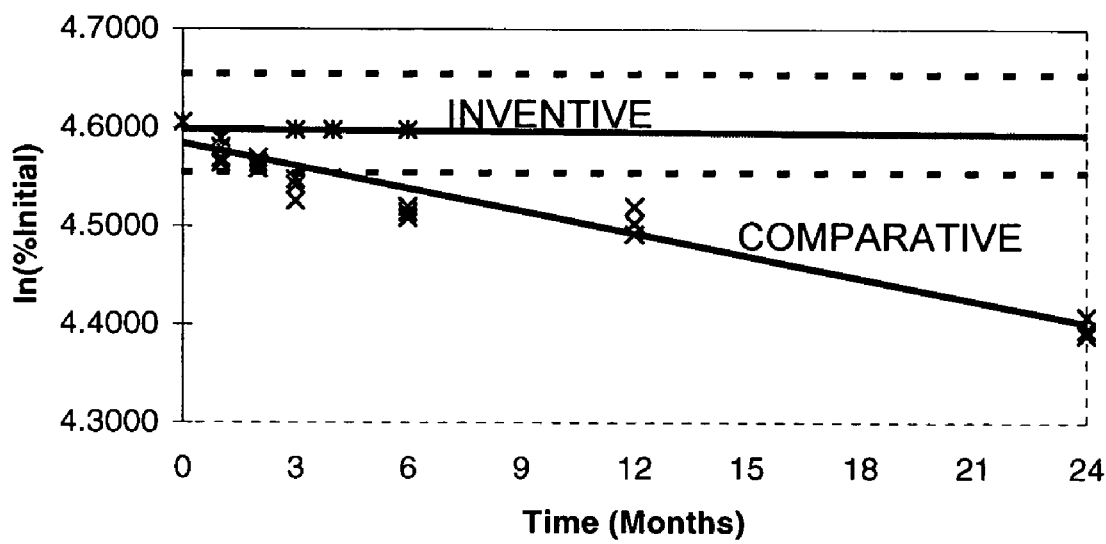
FIG. 2 shows the data for longer stability or shelf-life of the inventive composition as compared to a composition known in the art.

This example illustrates the longer stability or shelf-life of the inventive composition. FIG. 2 shows a comparison of the previous known composition ("comparative formulation") and the inventive composition. The dotted lines shown therein are the federal certified limits that define shelf-life as defined in 40 C.F.R. § 158.175 and in Table 1. As long as the pesticidal agent is within the dotted lines, it is within the certified limits and is a stable.

Note that there is a dramatic increase in stability with the inventive composition and process which has resulted in a remarkably different product with respect to conformance to the certified limits.

As shown in FIG. 2, the inventive composition stays within the certified limits at least to 3 months, at least to 6 months, at least to 9 months, at least to 12 months, 18 months, 24 months and up to 36 months, whereas the comparative formulation without a biopolymer is outside the certified limits after only 3 months.

Example 2

This example illustrates the increased stability of the inventive compositions.

Figure 3:
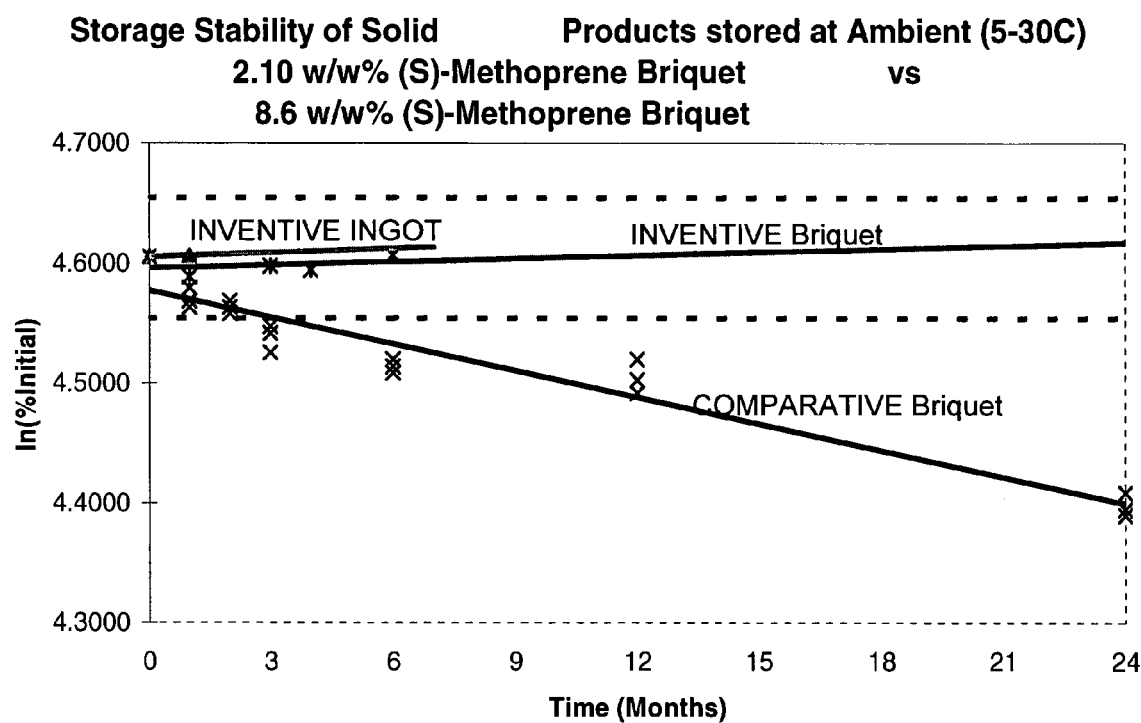
FIG. 3 shows a graph comparing the inventive composition Briquet versus the previous stability study for a comparative Briquet and inventive Ingot shaped product.

FIG. 3 shows a graph comparing the inventive formula for a Briquet versus data for a comparative Briquet made in accordance with U.S. Pat. No. 4,732,762 and the inventive Ingot shaped product. The dotted lines are the federal certified limits that define shelf-life. As long as the product is within the dotted lines, the product is within the certified limits and is a stable product. As such, the inventive formulation results in a product without an expiry date.

As shown in FIG. 3, the inventive composition has increased shelf-life. The inventive products were assayed and found to be within the established certified limits. The assay data for the inventive formulations is shown in Tables 2 and 3.

Inventive Ingot

Certified Limits:

1.99% (Minimum)

2.10% (Nominal)

2.21% (Maximum)

Label: 2.10% wt/wt % (S)-Methoprene

TABLE 2

| Time | Storage Condition | (S)-Methoprene (w/w %) | % Initial | Physical Appearance |
|---|---|---|---|---|
| Initial | Ambient | 2.04 | 100.0 | NVA |
| 1 MONTH | Ambient | 2.00 | 98.4 | NVA |
| 3 MONTHS | Ambient | 2.02 | 99.3 | NVA |
| 4 MONTHS | Ambient | 2.01 | 98.9 | NVA |
| 6 MONTHS | Ambient | 2.04 | 100.2 | NVA |

Inventive Briquet

Certified Limits:

8.19% (Minimum)

8.62% (Nominal)

9.05% (Maximum)

Label 8.62%

TABLE 3

| Time | Storage Condition | (S)-Methoprene (w/w %) | % Initial | Physical Appearance |
|---|---|---|---|---|
| Initial | Ambient | 7.97 | — | NVA |
| 4 Weeks | Ambient | 7.87 | 98.8 | NVA |
| 6 Weeks | Ambient | 7.84 | 98.4 | NVA |
| 11 Weeks | Ambient | 7.81 | 98.0 | NVA |

Example 3

This example illustrates that the inventive composition has increased hardness (e.g., tensile strength) and thus a slower release compared to the prior art.

The inventive formulation has increased hardness or compression strength compared to the prior art. The inventive formulation provides extended slow release parameters, e.g. they are harder because they dissolve more slowly, hence extending the utility and efficacy in the field. For example, the inventive formulation of the 30 day briquet lasts twice as long in the field compared to the prior art, delivering 60 days of efficacy. The biopolymer (e.g., polymeric gum) increases the formulation strength.

Formulation hardness is the physical strength measurement of the formulation. The resistance of a solid formulation to chipping, abrasion, or breakage under conditions of storage, transportation and handling before usage depends on its hardness, or "crushing strength." The solid formulation's "crushing" or "tensile" strength is defined as the force required to break a solid formulation by compression in the radial direction. It is typically measured using one of the many commonly available solid formulation hardness testers. For example, "Stokes" and "Monsanto" hardness testers measure the force required to break the solid formulation when the force generated by a coil spring is applied diametrically to the formulation. A "Strong-Cobb" hardness tester also measures the diametrically applied force required to break a solid formulation, the force applied by an air pump forcing a plunger against the formulation placed on an anvil. Electrically operated hardness testers, such as the Schleuniger apparatus (also known as a "Heberlein") can be used. In certain other instances, a penetrometer can be used.

Using the forgoing methods, the inventive compositions have increased "crushing" or "tensile" strength compared to the prior art.

Example 4

This example illustrates an inventive embodiment.

| Ingredient | % by weight |
|---|---|
| IGR | 1.0–10.0 |
| carrier | 1.0–10.0 |
| antioxidant | 0.01–0.1 |
| binder | 70–90 |
| biopolymer | 0.1–1.0 |
| water | 10–15 |

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A pesticide composition, said pesticide composition comprising:
    a pesticidal agent on a solid carrier, wherein the pesticidal agent is methoprene;
    a biopolymer;
    an effective amount of a plaster of paris to harden said composition, wherein said pesticidal agent maintains certified limits for at least 12 months; and wherein N is the nominal concentration of said pesticidal agent and the certified limits are as follows:

|  | Upper Limit | Lower Limit |
|---|---|---|
| $N \leq 1.0\%$ | $N + 10\% \, N$ | $N - 10\% \, N$ |
| $1.0\% < N \leq 20.0\%$ | $N + 5\% \, N$ | $N - 5\% \, N$ |
| $20.0\% < N \leq 100.0\%$ | $N + 3\% \, N$ | $N - 3\% \, N.$ |

2. The composition of claim 1, wherein the ratio of pesticide to solid carrier is from about 0.001 to about 30.0 w/w.

3. The composition of claim 2, wherein the ratio of pesticide to solid carrier is from about 0.01 to about 10.0 w/w.

4. The composition of claim 1, further comprising a surfactant.

5. The composition of claim 4, wherein said surfactant is a member selected from the group consisting of a nonionic ethoxylated alcohol and an ethoxylated substituted phenol.

6. The composition of claim 1, wherein said composition maintains certified limits for at least 24 months.

7. The composition of claim 1, wherein said solid carrier is selected from the group consisting of silica gel, sand, carbon, and combinations thereof.

8. The composition of claim 7, wherein said solid carrier is carbon.

9. The composition of claim 1, wherein said biopolymer is a polysaccharide.

10. The composition of claim 9, wherein said polysaccharide is a member selected from the group consisting of acacia, agar, alginate, guar, locust bean, tragacanth, xanthan, and combinations thereof.

11. The composition of claim 1, wherein said ratio of pesticidal agent to biopolymer is from about 1000:1 to about 1:1 w/w.

12. The composition of claim 11, wherein said ratio of pesticidal agent to biopolymer is from about 500:1 to about 1:1 w/w.

13. The composition of claim 11, wherein said ratio of pesticidal agent to biopolymer is from about 75:1 to about 1:1 w/w.

14. The composition of claim 1, further comprising an antioxidant.

15. The composition of claim 14, wherein said antioxidant is selected from the group consisting of Vitamin E, Vitamin A palmitate, ethoxyquin, propyl gallate, butylated hydroanisole (BHA), butylated hydroxytoluene (BHT), and combinations thereof.

* * * * *